United States Patent [19]
Pappas et al.

[11] Patent Number: 5,817,713
[45] Date of Patent: Oct. 6, 1998

[54] WATER SWELLABLE COATINGS AND METHOD OF MAKING SAME

[75] Inventors: Vincent J. Pappas, Lansdale; Louis A. Vitola, Ambler; Vernon Z. Detwiler, Telford, all of Pa.

[73] Assignee: Fiber-Line, Inc., Hatfield, Pa.

[21] Appl. No.: 588,944

[22] Filed: Jan. 19, 1996

[51] Int. Cl.$^6$ ............................... C08J 3/00; C08L 27/06
[52] U.S. Cl. .......................... 524/521; 524/297; 524/522
[58] Field of Search .................................. 524/522, 523, 524/297, 521

[56] References Cited

U.S. PATENT DOCUMENTS

| | | | |
|---|---|---|---|
| 3,940,532 | 2/1976 | Smith, II | 428/218 |
| 4,178,271 | 12/1979 | Busch et al. | 428/532 X |
| 4,304,812 | 12/1981 | Perkins | 428/247 |
| 4,402,789 | 9/1983 | Vexler | 162/106 |
| 4,436,857 | 3/1984 | Kuan et al. | 524/522 X |
| 4,503,184 | 3/1985 | Marongiu | 524/522 X |
| 4,533,524 | 8/1985 | Burba et al. | 427/372.2 |
| 4,913,517 | 4/1990 | Arroyo et al. | 350/96.23 |
| 5,032,462 | 7/1991 | Kim | 428/501 |
| 5,091,455 | 2/1992 | Blank et al. | 524/297 |
| 5,102,946 | 4/1992 | Chen et al. | 524/527 |
| 5,139,841 | 8/1992 | Makoui et al. | 428/109 |
| 5,202,381 | 4/1993 | Parker | 524/522 X |
| 5,306,867 | 4/1994 | Connole et al. | 523/173 X |
| 5,321,788 | 6/1994 | Arroyo et al. | 252/70 |
| 5,342,686 | 8/1994 | Guersen et al. | 428/378 |
| 5,366,738 | 11/1994 | Rork et al. | 424/473 |
| 5,389,442 | 2/1995 | Arroyo et al. | 428/396 |
| 5,476,718 | 12/1995 | Ichizuka et al. | 524/507 X |
| 5,478,882 | 12/1995 | Summers et al. | 524/569 |
| 5,505,836 | 4/1996 | Miyahara et al. | 204/418 |
| 5,543,154 | 8/1996 | Rork et al. | 424/473 |

OTHER PUBLICATIONS

Stockhausen, Favor C, Absorbent Polymers, Undated, Product Information Sheet, (2 pages).

Stockhausen, Favor C, Absorbent Polymers, Undated, Product Information Sheet, (3 pages).

Stockhausen, Favor C, Undated, (1 page).

Stockhausen, The Absorber, News About Absorbent Polymers, Brochure, Jan. 1992, (pp. 1–15).

Hoechst Celanese, Material Safety Data Sheet, Undated, Sanwet IM–3900, Starch Grafted Sodium Polyacrylate, (1 page).

Chemdal Corporation, Material Safety Data Sheet, Undated, Aridall 1125J, Potassium Polyacrylate, lightly crosslinked, (2 pages).

AQUA KEEP J–550, J–550–C, J–550–F, J–550–SF Superabsorbent Polymers, Poly(sodium acrylate) hompolymer or sodium salt of polyacrylic acid, OSHA Standard 29 CFR 1910.1200, Material Safety Data Sheet, Dated Jun. 17, 1993, (3 pages).

Dow Chemical U.S.A, Material Safety Data Sheet, XU 43408.00 Experimental Absorbent Polymer "DryTech", Partial Sodium Salt of Crosslinked Polypropenoic Acid, (1 page).

Protecting Buried Cables from Moisture, High Performance Textiles, Oct. 1994, (1 page).

Primary Examiner—Judy M. Reddick
Attorney, Agent, or Firm—Panitch Schwarze Jacobs & Nadel, P.C.

[57] ABSTRACT

A method for forming a water swellable coating and a water swellable coating for forming a coated substrate are provided. The water swellable coatings are semi-gel dispersions of particulate superabsorbent polymer in a polyvinyl chloride plastisol. A dispersion is formed from the polymer and plastisol, then contacted with a substrate and heat cured to a semi-gel state. The coatings are capable of swelling in the presence of water to protect the substrates from water penetration, block water from penetrating the coatings to reach other substrates or to retain water to prevent leakage.

11 Claims, 5 Drawing Sheets

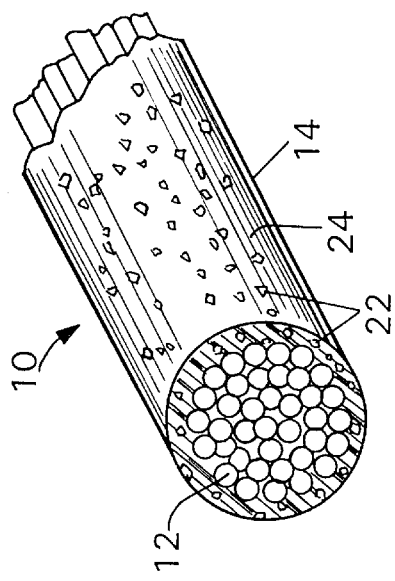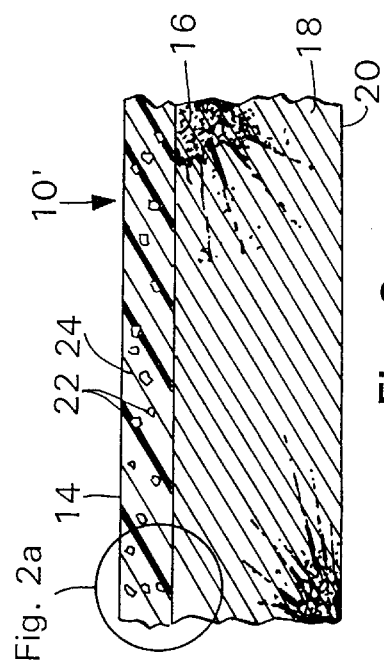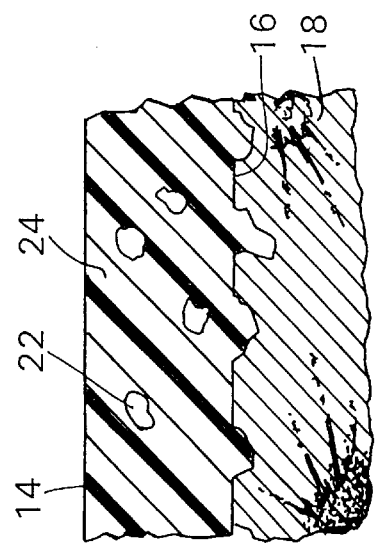

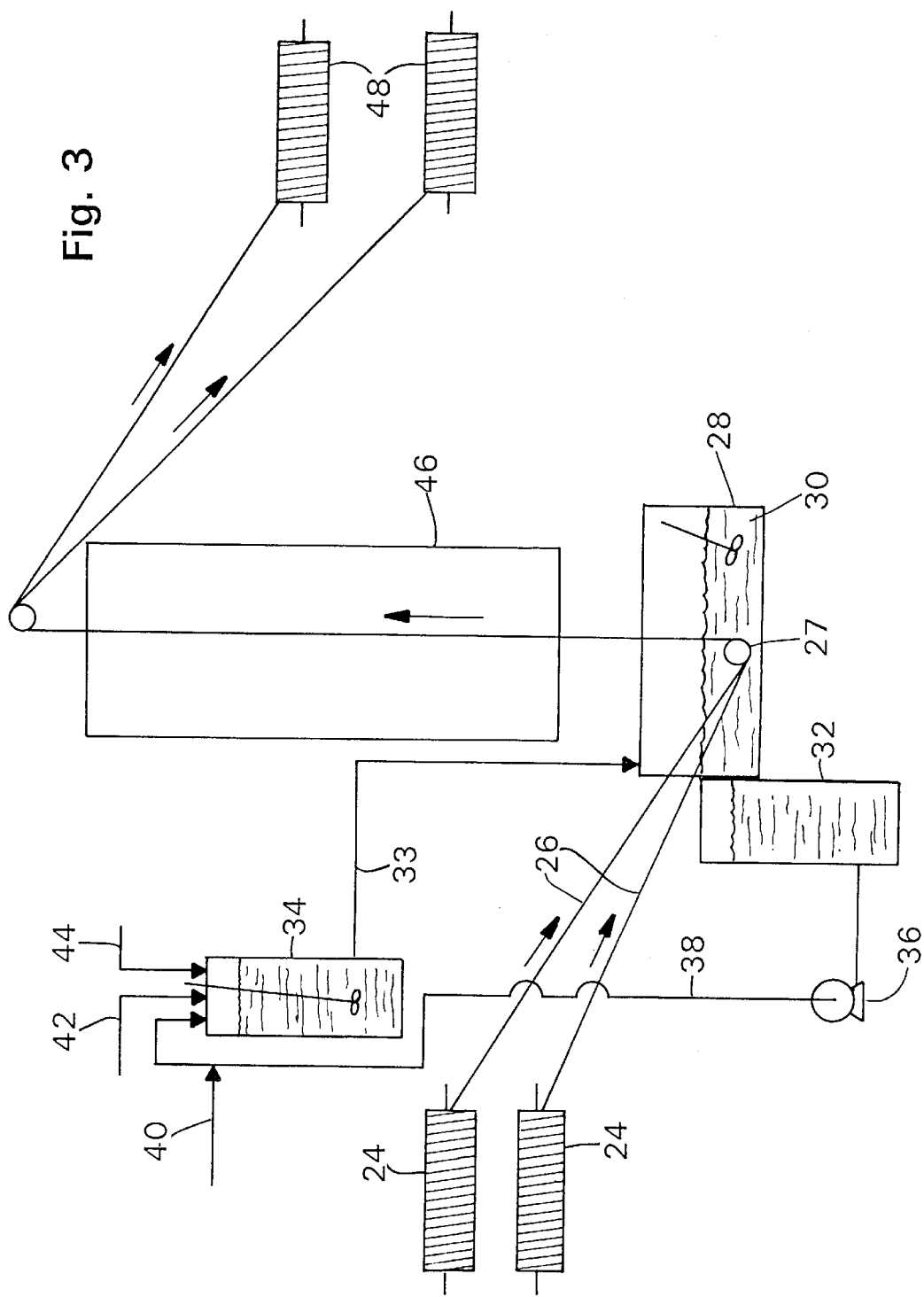

WATER SWELLABLE COATINGS AND METHOD OF MAKING SAME

FIELD OF THE INVENTION

The present invention relates to the field of water swellable coatings, more particularly to semi-gelled water swellable coatings formed from a dispersion of superabsorbent particulate polymer in a liquid polyvinyl chloride plastisol.

BACKGROUND OF THE INVENTION

Super absorbent polymers (SAP) are compounds capable of swelling to many times their original weight by absorbing water. SAPs are used, among other things, as an absorbing compound for baby diapers, in protecting power and communication cables, in agriculture for use in increasing the capability of soil to retain moisture and nutrients, and in the hygienic packaging of food products with absorbent pads. SAPs swell upon exposure to water, and in many instances, are capable of absorbing up to 500 times their weight in water. The SAPs are typically used in powder form or in a composite form in which SAP particles are blended with fine fibers and then entrapped within a fibrous mat.

In the past, attempts have been made to use the SAPs to form coatings on synthetic fiber used in the manufacturing of cable, such as fiber optic cable. The coated synthetic fiber was used in place of preexisting synthetic fiber components for cable. The intention was that the coating would swell upon exposure to water and fill gaps in the cable rendering the cable watertight to protect the fiber optic component. The present inventors attempted to provide SAPs to the cable in the form of a fully fused solid dispersion of SAP in a polyvinyl chloride (PVC) plastisol coated fiber. The PVC plastisol included PVC resin in suspension in a plasticizer. However, the fully fused dispersion in fiber optic cables did not perform satisfactorily, because the SAPs do not swell at a sufficient rate when subjected to pressurized water. The fused, solid PVC plastisol matrix functions to restrain the ability of the SAP to swell.

To form these dispersions, SAP powder was blended with liquid PVC plastisol formulation. The plastisol formulation was converted from its liquid state to a homogeneous solid plastisol through fusion of the plasticizer and PVC at elevated fusion temperatures of about 121° to about 170° C. or more to fully cure the dispersion. Synthetic fibers were coated with the fused dispersion and then used in the manufacture of fiber optic cable as a filler, binder, strength member and similar uses.

A further application of SAP in a coating formulation includes an emulsion of SAP in an oil-in-water emulsion as described in U.S. Pat. No. 5,342,686. This coating formulation may be used for light coatings on KEVLAR substrates, but is not suitable for heavier SAP coatings, such as those required to block penetration of water into coaxial cable. Further, the emulsion uses solvents which may be detrimental in many coating applications and/or harmful to the enviroment.

While the SAP/PVC dispersions for use as swellable coatings were essentially comparable with other prior art fillers, a need in the art remains for an improved SAP coating composition which is capable of using more of the swelling capabilities of the SAPs and expanding the potential uses for SAP coatings. There is also a need in the art for a method of forming an SAP coating composition which provides maximum water absorption properties. In addition, it would be desirable to achieve a coating composition useful on synthetic fibers, synthetic woven and unwoven fabrics and other substrates which swell at a rate sufficient to protect the substrate from penetration of water.

SUMMARY OF THE INVENTION

The invention includes a water swellable coating, and a coated or at least partially impregnated substrate which includes a water swellable coating on a surface, or within voids, of the substrate. The coating comprises a semi-gel dispersion of a particulate SAP in a PVC plastisol, and substantially blocks the penetration of water through the coating and/or retains water. The present invention also includes a method for making a coated substrate.

The method includes preparing a dispersion including a particulate SAP and a liquid plastisol which includes a PVC resin and a plasticizer. The substrate is contacted with the dispersion to form a coating layer on the substrate, or to at least partially impregnate the substrate. The coating layer is heat cured for a period of time sufficient to form a water swellable, semi-gel coating layer on the substrate. The coating layer may at least partially impregnate the substrate.

BRIEF DESCRIPTION OF THE DRAWINGS

The following description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings, like numerals are used to indicate like elements throughout. In the drawings:

FIG. 1 is a partially broken away perspective view of a synthetic fiber coated in accordance with the present invention;

FIG. 2 is a cross-sectional view of a synthetic fabric coated in accordance with the present invention;

FIG. 2a is a partially broken away greatly enlarged sectional view of a portion of the sythetic fabric of FIG. 2;

FIG. 3 is a schematic representation of a method for making a coated fiber in accordance with the present invention;

DETAILED DESCRIPTION OF PREFERRED EMBODIMENTS

Figure 4:
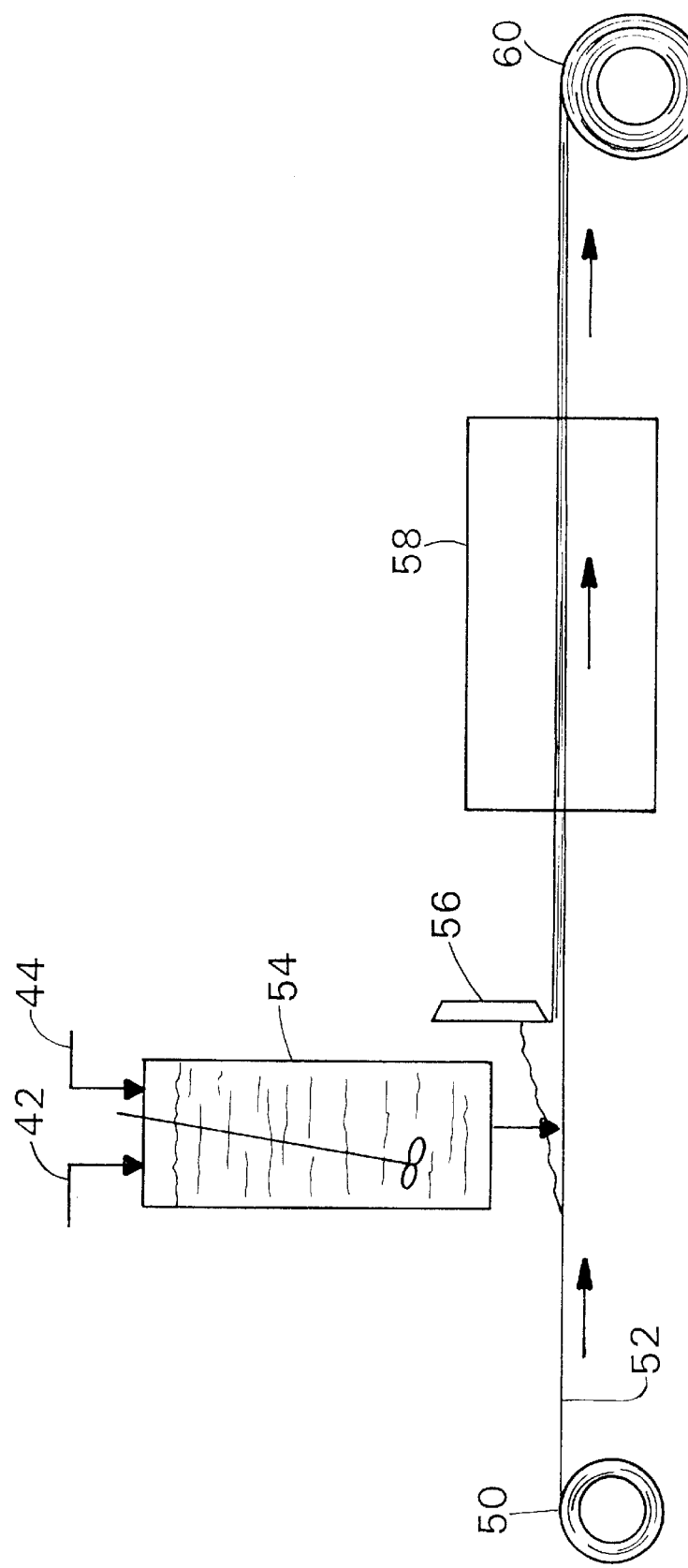
FIG. 4 is a schematic representation of a method for making a coated fabric in accordance with the present invention.

Certain terminology is used in the following description for convenience only and is not limiting. The words "right," "left," "lower" and "upper," designate directions in the drawings to which reference is made. The terminology includes the words above specifically mentioned, derivatives thereof, and words of similar import.

The coatings of the present invention may be used on a wide variety of substrates, including, for example, synthetic fiber materials, such as polyamide, polyaramid, polyester, fiberglass, carbon, polyolefin, polyacrylic and rayon; natural fibers such as cotton, metallic fibers such as carbon and steel fibers, synthetic woven and nonwoven fabrics formed of materials such as those mentioned with respect synthetic fibers which may be used for making filters, awnings, carpets and textiles; synthetic films, polymeric components, metals, metal alloys, wood, concrete, composites, paper and the like. The coatings may be used on any substrate to which the coatings will sufficiently adhere such that they do not easily peel off. Further, such coatings are useful in a wide variety of applications in which it is important to prevent water or other liquids from passing through or reaching a substrate.

Such applications include the coating of coaxial cable to render the cable watertight, the coating of fiber fillers for use inside cable to prevent water from damaging fiber optics, or the coating of fabrics or films to prevent water from passing through a laminate structure. Due to the wide variety of uses for the present coatings, for the purpose of describing the preferred embodiments of practicing the present invention and the best mode, the detailed description is directed to the preferred embodiments of using the coating of the present invention on synthetic fiber material and a synthetic fabric substrates. However, it will be understood from this disclosure that the present invention is not limited to use on these particular substrates.

While the water swellable coatings are described herein as capable of forming a coating layer on a substrate, it will be understood from this disclosure that, in many coating applications, the coating will at least partially impregnate a substrate, such as a fiber material, to form a water swellable impregnate within at least an outer portion of the substrate. As such, use of the terminology "coating" should be interpreted to include within its meaning surface coating and/or at least partially impregnating a substrate with the semi-gel dispersion as described below.

Referring now to the drawings in detail, there is shown in FIG. 1 a coated substrate, generally designated as 10, including a fiber substrate 12 and a water swellable coating 14 in accordance with the present invention. In FIG. 2, a water swellable coating 14 is provided to one exterior surface 16 of a synthetic fabric substrate 18 to form a coated substrate 10' in accordance with the present invention. It will be understood by those of ordinary skill in the art, from this disclosure, that both surfaces 16, 20 of the fabric 18 may be coated with a water swellable coating according to the present invention. As shown in FIG. 2a, the fabric 18 may contain voids 21 which can be penetrated, or impregnated, by the coating 14. The water swellable coating 14 substantially blocks the penetration of water through the coating to protect the substrate. As shown in FIGS. 1 and 2, the coating 14 includes a semi-gel dispersion of a particulate SAP 22 in a PVC plastisol 24. The particulate polymer 22 is shown greatly enlarged for descriptive purposes.

The coating may partially impregnate the substrate, as shown in FIG. 2a, or it may impregnate a fiber bundle in voids between fibers. The coating further may function to protect the substrate which it coats, or to protect another substrate, for example, the coating may be used on a fibrous filler substrate which is used to protect a further substrate such as a fiber optic core. The coatings on the small filler fibers swell upon exposure to water and expand to block water penetrable gaps between the coated filler fibers. The coatings retain water which has already filled the gaps between the filler fibers and retains that water while preventing further water penetration. It is in applications such as this that the absorption rate of the coating is important. If the coating does not absorb water fast enough, it will penetrate the gaps between the coating harming the fiber optic core before the coating swells to its full potential.

A further function of such a coating is to act as a water retaining coating. An example of such a water retaining application includes coating a fiber which may be used in the manufacture of diapers. The fiber would swell to retain water and also function to block water from passing out of the diaper.

The coating includes a semi-gel dispersion of a particulate SAP in a PVC plastisol. The SAP may be any of various superabsorbent polymers having an average particle size of about 500 microns, where average particle size is measured in the largest dimension of the particle. The particle size may be smaller or larger depending upon the particular application for the coating. Preferably, the average particle size is from about 1 to about 500 microns. and the polymer is in a powder form. In addition, the polymers are preferably at least partially cross-linked. Suitable preferred SAPs include salts of polyacrylate-based polymers. The salts which may be used in forming the SAPs include sodium, potassium and ammonium. The preferred SAPs for use in the present invention include homopolymers and copolymers of sodium and potassium polyacrylates. Other useful polymers include starch grafted sodium polyacrylate and partial sodium salt of polypropenoic acid.

When coating a substrate such as a synthetic fiber, cord, strand, rope, braid or any other synthetic fiber material or a fine synthetic fabric which will be exposed to water or other liquid environments, preferably the SAP is a sodium polyacrylate homopolymer with an average particle size of no greater than about 100 microns. Such polymers can be found commercially as CABLOC 80HS available from Stockhausen Inc., Greensboro, N.C.; AQUA KEEP J-550-SF available from Sumitomo Seika Chemical Company, Ltd., Japan; and SANWET IM1000F available from Hoechst Celanese.

When coating a heavier substrate, for example a heavier synthetic fabric, or for coating substrates such as synthetic fiber materials or fine synthetic fabrics which will be exposed to a higher electrolytic concentration in the surrounding liquid to be absorbed, for example salt water or waste water with a significant ion content, the SAP preferably has a larger average particle size of from about 100 to about 300 microns. Suitable SAPs useful in such applications include potassium copolymers of polyacrylate and polyacrylamide in which the copolymer is crosslinked. Suitable commercial SAPs for such use include CABLOC 100F available from Stockhausen, Inc., Greensboro, N.C.

The SAPs according to the present invention are hydrophilic polymers capable of absorbing and retaining a comparatively large quantity of water. The polymers include water binding groups, for example carboxylic acid groups. The salt ions of the acrylate-based polymers, as used in the present invention, are located at the carboxylic acid groups pendant from the polymer carbon backbone. The carboxylic acid groups are solvated when contacted with water, or other aqueous liquids, forming many charged ionic groups which repel each other. The polymer chain, in the presence of water, or other liquid, expands and unfolds such that it can absorb more liquid. While such a polymer may otherwise dissolve, a slight crosslinking present in the SAP chains used in the present invention prevents them from completely dissolving. When used in powder form, the SAPs exposed to water contain the water and form a gel.

In the coating according to the present invention, the SAP is dispersed in a liquid polyvinyl plastisol. The liquid plastisol includes a PVC resin and a plasticizer. The liquid plastisol may be purchased commercially as a plastisol formulation or independently synthesized. Preferably, for most fiber coating applications, the plastisol used, if fully fused to a solid, would have a Shore hardness of from about 10 Shore A to about 90 Shore A hardness, preferably about 50 Shore A. It is also preferred that the liquid plastisol used have a relatively low viscosity as the dispersion of the particulate superabsorbent polymer in the plastisol will significantly increase viscosity. As such, the liquid plastisol preferably has the consistency of a pourable liquid and a viscosity of from about 500 to about 40,000 cp, preferably about 1,000 to 4,000 cp.

While an organosol may be used, or the viscosity of the plastisol adjusted with an organic solvent which is later volatilized, it is not preferred to use solvent based materials in the present invention due to considerations of toxicity, volatility and environmental impact of solvent-containing compounds.

The resin within the liquid plastisol may be any PVC dispersion resin or a blend of PVC dispersion and blending resins as long as the viscosity criteria of the plastisol are satisfied.

The plasticizer may also be any suitable plasticizer useful in PVC plastisols, however, the plasticizer must be selected to meet the viscosity criteria for the plastisol. Suitable plasticizers for the liquid plastisol to be used in the present invention include di-2-ethylhexyl phthalate (DOP), dihexyl phthalates, dibutyl phthalates, alcohol phthalates, dioctyl adipate (DOA), phosphate esters such as tricresyl phosphate, octyldiphenyl phosphate and trioctyl phosphate, dioctyl adipate, dioctyl sebacate, trioctyl trimellitate, and triisooctyl trimellitate, as well as blends or mixtures of these and other similar plasticizers. Preferably, the plasticizer used is DOP or DOA.

The plasticizer and PVC resin are preferably present in the liquid plastisol in a range of weight percentage ratios of resin to plasticizer of from about 0.25:1 to about 3:1, more preferably about 1:1. It will be understood from this disclosure that more or less resin or plasticizer can be provided for variations in the resulting properties of the present SAP dispersion as long as the resulting coating can be provided in a semi-gel form.

The plastisol may optionally include additives such as secondary plasticizers, flame retardants, stabilizers, fillers, colorants, viscosity modifiers, foaming agents and combinations of these additives.

Suitable secondary plasticizers may include, for example, those listed above, aliphatic hydrocarbons, epoxidized soya, oils and/or other known plasticizers.

Stabilizers are preferably capable of neutralizing hydrogen chloride, a decomposition product of PVC. Suitable stabilizers include, for example, mixed metal salts, such as barium-cadmium-zinc-based, barium-cadmium-based and cadmium-zinc-based stabilizers and organic tin stabilizers. Preferably, the mixed metal salt stabilizers are used. Light and UV stabilizers, such as 2-hydrobenzophenones, aryl-substituted acrylates and p-aminobenzoates can also be provided.

Other suitable additives include antimony derivative flame retardants, colorants such as pigments, titanium dioxide, zinc oxide and carbon black, and fillers such as calcium carbonate, asbestos, clay, talc, silica and the like. Viscosity modifying additives may also be provided as long as the resulting plastisol has a viscosity suitable for forming the dispersion in accordance with the present invention.

If the dispersion is to be foamed for other water swellable applications, foaming agents can be added and the dispersion foamed by a suitable foaming method.

The additives should be provided to the plastisol in amounts of from about 0.1 to about 10 parts by weight per hundred parts by weight of plastisol.

The dispersion of SAP in the liquid plastisol should include from about 10 weight percent to about 50 weight percent of particulate SAP. If more than about 50 weight percent SAP is provided to the dispersion, the dispersion consistency is too dry or paste-like, and less than 10 weight percent is not sufficient SAP to effectively swell. More preferably, the dispersion includes about 30 weight percent SAP.

The coating of the present invention is a semi-gel dispersion. Once the particulate SAP is dispersed in the liquid plastisol, the dispersion becomes a semi-gel by heat curing for a period of time sufficient to partially gel the plasticizer and the PVC resin.

PVC resin plastisols generally fuse at temperatures between 121°–177° C. when a homogeneous "hot melt" stage is achieved. To form a solid plastisol, the hot melt phase is cooled to below a temperature of about 50°–60° C. Such a plastisol is fully cured after fusion. As temperature increases, PVC plastisol liquid goes through gelation and then fusion by passing through a series of polymer stages, including wetting of the suspended polymer particles in the plastisol liquid by the plasticizer, diffusion of the plasticizer into the particles, disappearance of boundaries between the particles, flowing together of the PVC polymer and melting of the crystallite structure with molecular flow achieved.

In the SAP dispersion of the present invention, as temperature increases, the plastisol begins to undergo the stages described above in the following approximate increments: (A) at temperatures up to about 35° C., the plasticizer wets the PVC particles; (B) at temperatures between about 35° C. and 50° C., the plasticizer diffuses into the resin particles; (C) at temperatures between about 50° C. and 90° C., the particle boundaries begin to disappear and the PVC flows together; and (D) at temperatures between about 90° C. and 170° C., the crystallites of PVC polymer fuse together.

The level of gellation is controlled in forming the present water swellable coatings to between stages (B) and (D) above. Between these phases, the coating partially undergoes gellation and has not yet fused such that a "semi-gel" phase of the dispersion is achieved. If the process were continued to full fusion and the resin cured in the manner of forming PVC plastisols generally, and in the manner of prior art attempts to form water swellable coatings, the water swellable properties would be detrimentally affected. The resulting coated substrates had a slow rate of absorption and low absorption capacity. Coated fibers exhibited high yarn stiffness and reduced yarn break strength.

In the present invention, by forming a semi-gel dispersion, the water swellable coatings achieve faster rates of absorption, and higher absorption capacities in comparison with prior art fully fused coatings. Further, water swellable yarns formed with the present coatings have increased flexibility and higher breaking strength in comparison with prior art coatings.

The water absorption capacity of the coatings are measured by submerging a layer of coating in distilled water and determining the weight of water absorbed after the elapse of a specific period of time. The weight of water is divided by the weight of the coating to provide the absorption capacity for that time period. The absorption rate is determined as the absorption capacity divided by the length of time of exposure. For a 0.011 inch thick planar layer of coating, the thickness being measured in a direction perpendicular to the plane of the layer, the absorption capacity is preferably at least about 34 g water/g coating in distilled water after a 5 minute period. More preferably, the coatings achieve an absorption capacity of at least about 40 g water/g coating for a 5 minute period of exposure of a 0.011 inch thick sample.

On coated substrates, the absorption capacity is measured in terms of the weight of water absorbed in grams divided by the weight of the coated substrate after the elapse of a specific period of time. The absorption rate is then determined by dividing the absorption capacity by the time of exposure.

The semi-gel coating when applied to substrates such as fiber, yarn, braid and the like as described above, provides a softer, more flexible coating than a fully fused coating. The semi-gel coated yarn exhibits a relatively flat cross-section in comparison with a fully-fused coated yarn which exhibits a harder, stiffer coating having a rounder or oval cross-section. The flat yarn cross-section is beneficial in applications such as a binder yarn for fiber optic cables as the flat profile generally does not interfere with the uniformity of the cable diameter. The lower stiffness of the semi-gel coating also helps to minimize the risk of line breakage in the cable as it does not tend to spring from the line in the manner of prior art coated fillers.

The reduced break strength of yarn coated by the present invention is most likely the result of the stiffer coating. In addition, due to the lower % elongation, and lower stiffness, the present invention provides more material for the same cost by having a higher yield as measured in length of yarn/unit weight.

When the plastisol is taken to the semi-gel state, upon heat curing, the plastisol does not age harden such that it remains in the same semi-gel state as processed. The semi-gel matrix enables the SAP to expand to achieve high levels of swelling in the presence of water or other aqueous liquids. The SAP can then perform its function of hydrogen bonding with the water or other liquid to retain the water and substantially block further penetration through the coating to the substrate or through voids between coated substrates which surround a water-sensitive material, such as the fiber optic cable filler described above. The SAP can also function merely to retain water in an absorbency application as in baby diapers.

The method of forming a coated substrate in accordance with the present invention will now be described with respect to the coating of a synthetic fiber material and a fabric referring to FIGS. 3 and 4. With reference to FIG. 3, one or more windings 24 of a synthetic fiber material 26 are drawn, under tension, by any suitable method, over a stationary bar 27 through a bath 28 of a dispersion 30 of particulate SAP in a liquid PVC plastisol. Additional stationary bars may be provided, or the stationary bar 27 may be replaced by one or more rollers. However, a stationary bar 27 is preferred to rollers to minimize fiber breakage. Preferably the dispersion bath 28 is continuously agitated to provide uniform dispersion to the fiber 26.

The dispersion 30 continuously overflows the bath 28 into a holding tank 32 and is continuously supplied to the bath 28 by gravity feed through line 33 from feed tank 34. The dispersion is pumped by a pump 36 through line 38 to the feed tank 34 and recirculated to the bath 28. In the coating of fiber materials, the plastisol in the bath 28 tends to be depleted. The rate of depletion of the plastisol in the bath is monitored by evaluating the absorption capacity of the material in the holding tank 32. The plastisol in the dispersion to be recirculated from the holding tank is replenished by providing an amount of plastisol to the feed tank 34 through line 40 based on the absorption capacity of the dispersion in the holding tank 32. The absorption capacity increases as the viscosity increases. Viscosity increases as the concentration of plastisol decreases in the dispersion in comparison to the concentration of SAP. As such, the absorption capacity is a preferred criteria for evaluating the rate of plastisol depletion. Viscosity may be directly monitored, but is generally not as accurate in determining the appropriate rate of plastisol depletion. By adding the plastisol to the feed tank 34 at a rate proportional to the rate of depletion, a substantially constant concentration of resin is maintained in the feed dispersion.

When beginning the method, the dispersion is formed in the feed tank by providing the particulate SAP 42 gradually to the liquid PVC plastisol 44, while providing continuous agitation to the plastisol dispersion in the feed tank 34. The SAP is preferably added at an average rate of about 20 to about 25 lb particulate polymer, preferably in the form of a powder, per minute. The rate of addition may vary in accordance with the size of the feed tank 34 and amounts of components used. The dispersion is preferably mixed by a heavy duty high torque mixer at a low speed of about 100 to about 1,500 rpm, preferably at a rate of about 750 rpm.

The fiber leaves the bath 28 with a coating and passes through an oven 46. Excess plastisol is preferably wiped from the fiber by use of a die, pad, roll or other suitable means. The oven may be a convection, conduction or infrared oven, for example. Preferably, an infrared oven is used having elements capable of temperatures of about 1,000° F. (538° C.). The oven chamber achieves an average ambient temperature between the elements of from about 200° F. (93° C.) to about 450° F. (232° C.). The temperature of the oven and the residence time in the oven are controlled to maintain a coating temperature of between about 50° C. to about 90° C., depending upon the PVC plastisol used, to achieve a semi-gel state for the PVC plastisol. Residence time in the oven is controlled by varying the speed of the fiber 26. Preferably, the fiber speed is controlled to between 55 ft/min and 65 ft/min. The fiber leaves the top of the oven after heat curing the coating to a semi-gel state and is wound up as a coated substrate on take-up rolls 48. A plurality of feed rolls 24 and take-up rolls 48 may be used in the present method for providing a water swellable coating. In addition, more than one oven, bath, holding tank and feed tank may be provided. It will be understood by one of ordinary skill in the art that the fiber coating process may be varied as long as viscosity, resin concentration, SAP concentration, fiber speed and oven temperature are adequately controlled to form a semi-gel coating on the fiber.

In FIG. 4, a roll 50 of synthetic fabric 52 is unwound, under tension, by any suitable method and drawn below a feed tank 54 to provide a continuous flow of a dispersion of a particulate SAP in a liquid polyvinyl resin dispersion as described above to the upper surface of the fabric 52. The feed tank 54 is subject to continuous agitation under low shear conditions, and the dispersion is formed, as described above with respect to the method shown in FIG. 3 and the coatings of the present invention. The dispersion is smoothed by a doctor blade 56, or similar smoothing apparatus, to provide a smooth coating to the fabric 52. The fabric is then drawn through an oven 58, such as that described above, wherein the temperature of the oven and the speed of the fabric are controlled to provide a semi-gel cure to the coating. The coated fabric leaves the oven and is wound on take-up roll 60 as shown.

The method for forming a coated fabric may be varied, for example, to provide coating to both sides of the fabric by pulling the fabric through a bath and smoothing the coating with opposing tension rolls, however, the coating parameters must be controlled to provide a semi-gel coating to the fabric.

The invention will now be described in more detail with respect to the following specific, non-limiting examples:

EXAMPLE I

Figure 5:
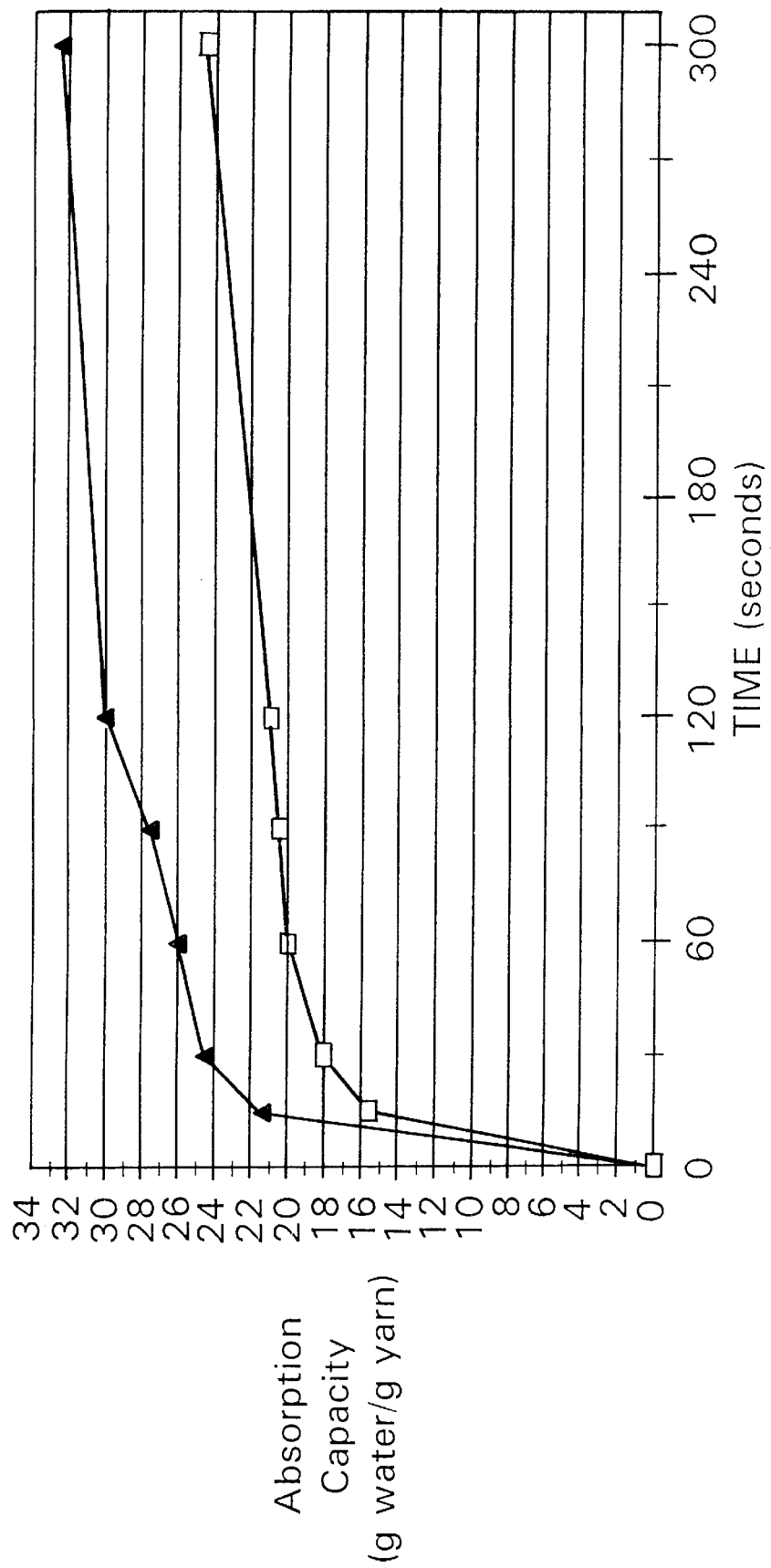
FIG. 5 is a plot of absorption capacity of water swellable coated polyester yarn in distilled water against time for both a prior art fully fused coating —■— and a semi-gel coating —▲— according to the invention.

Polyester yarn samples (Experimental Samples 1–6) coated with semi-gel coatings of a dispersion including 30 weight percent CABLOC 80HS and 70 weight percent Plastomeric DBX 3590N PVC were measured for absorption capacity in distilled water as measured in g distilled water/g coated substrate. The yarn samples were cut into lengths of about 1 inch and weighed. About 2.00±0.01 g of the yarn are stirred with 100 ml of distilled water for 10 min. The mixture is filtered for 15 minutes and the amount of water recovered is measured. The absorption capacity is calculated by dividing the difference of the amount of water recovered from 100 by the weight of the yarn. The same test was performed for the same type of polyester yarn (Comparative Samples 1–6) coated with fully fused coatings of the same dispersion, fused at a temperature of 170° C. for 5 min an air circulating oven. The absorption capacity was measured for the Comparative Samples in the same manner as for the Experimental Samples. The results of these tests showing the absorption capacity at various time intervals appears below in Table I. A comparison of the increase in absorption rate of the Experimental Samples over the Comparative Samples of a prior art fully fused coating is shown graphically in FIG. 5 where the triangular data points —▲— present the Experimental Samples and the square data points —■— represent the Comparative Samples.

TABLE I

| Sample No. | Time (sec) | Absorption Capacity Experimental Samples (g water/g yarn) | Absorption Capacity Comparative Samples (g water/g yarn) |
|---|---|---|---|
| 1 | 15 | 21.5 | 15.5 |
| 2 | 30 | 24.5 | 18.0 |
| 3 | 60 | 26.0 | 20.0 |
| 4 | 90 | 27.5 | 20.5 |
| 5 | 120 | 30.0 | 21.0 |
| 6 | 300 | 32.5 | 24.5 |

The results clearly show the significant increase in absorption rate and absorption capacity of the water swellable yarn made in accordance with the invention and the prior art water swellable yarn.

EXAMPLE II 150 lb of CABLOC 80HS were gradually added to a 55 gallon tank equipped with a low shear Lightnin mixer, over a 15 minute period, to 350 gallons of a dispersion of liquid PLASTOMERIC DBX 3590 N while continuously mixing the dispersion. The weight percentage ratio of resin to plasticizer in the plastisol was approximately 1:1. The dispersion was continuously stirred at 750 rpm. 64 rolls of polyester were unwound and pulled at a rate of 60 ft/min through a bath of the dispersion. The absorption capacity was maintained at a minimum of 30 times for distilled water. The rate of depletion of plastisol was determined to be 20 lb/hr. A corresponding amount of plastisol was added to the tank to provide a substantially constant concentration of plastisol in the tank. The bath was continuously agitated at a rate of 100 rpm. The coated polyester fiber was pulled through a Glenro RADPLANE infrared oven having elements at 1000° F. (537° C.). The residence time in the oven was 5 seconds and the coating was cured to a semi-gel state. The coated polyester was wound on 64 take-up rolls. The coated polyester fiber had a minimum absorption capacity of 12 g distilled water/g coated fiber when submerged in distilled water for 5 min, a breaking strength of 35 lb and a % elongation of 15%.

EXAMPLE III

A coaxial cable having a water swellable coating was formed by a dip coating process using the dispersion of Example II and curing the coaxial cable in the same oven as used in Example II at a temperature 1100° F. (593° C.) by pulling the cable through the oven at a rate of 15 ft/min. The coating on the coaxial cable exhibited an absorption capacity of 4.4 g distilled water/g coated coaxial cable when submerged in distilled water for 5 min.

EXAMPLE IV

A section of synthetic/cotton blend woven fabric 5 in wide×5 in long×0.010 in thick was coated with the dispersion of Example II. The excess dispersion was scraped with a steel blade which also smoothed the coating on one side of the fabric. The coated fabric was heated in an air circulating oven for 5 min at 140° C. to provide a coated fabric having a thickness of 0.012 in, corresponding to a coating thickness of 0.002 in. The coated fabric sample was 67 percent by weight fabric and 33 percent by weight coating. The absorption capacity of the coated fabric after 10 minutes in distilled water was 22 g distilled water/g coated fabric.

EXAMPLE V

Two bobbins of coated polyester fiber were made, an Experimental bobbin having the coating as described in the Experimental Samples of Example I and a Comparative bobbin having the coating as described in the Comparative Samples of Example I. Samples 7–11 were taken from each bobbin and tested for break strength and elongation in accordance with ASTM D2256. The results appear in Table II below and include the mean value and standard deviation (SD) for Experimental Samples 7–11 and Comparative Samples 7–11.

TABLE II

| | Experimental Samples | | Comparative Samples | |
|---|---|---|---|---|
| Sample | Break Strength (lb) | Elongation (%) | Break Strength (lb) | Elongation (%) |
| 7 | 35.0 | 9.8 | 32.0 | 16.1 |
| 8 | 36.0 | 10.4 | 33.0 | 16.5 |
| 9 | 37.0 | 11.0 | 32.0 | 16.1 |
| 10 | 36.0 | 10.2 | 34.0 | 16.9 |
| 11 | 37.0 | 10.6 | 33.0 | 16.5 |
| Mean | 36.2 | 10.4 | 32.8 | 16.4 |
| SD | 0.84 | 0.45 | 0.84 | 0.33 |

The results show that the break strength of the Experimental Samples is about 10% greater than the Comparative Samples made in accordance with prior art fully fused coatings. Further, the Experimental Samples show a 36% lower elongation percent at break than the Comparative Samples.

EXAMPLE VI

Example I was repeated for Experimental Samples 12–17, with the exception that the absorption capacity was measured in tap water to show the effect of electrolytes in tap water on absorption capacity and absorption rate. The absorption capacity results appear in Table III below, and the increase in absorption rate achieved by the Experimental Samples are shown in FIG. 6, where the triangular data points —▲— represent the Experimental Samples and the square data —■— points represent the Comparative Samples.

TABLE III

| Sample No. | Time (sec) | Absorption Capacity Experimental Samples (g water/g yarn) | Absorption Capacity Comparative Samples (g water/g yarn) |
|---|---|---|---|
| 12 | 30 | 12.3 | 6.7 |
| 13 | 60 | 13.0 | 10.7 |
| 14 | 90 | 14.7 | 11.3 |
| 15 | 120 | 15.7 | 12.0 |
| 16 | 300 | 17.3 | 13.3 |
| 17 | 600 | 18.0 | 14.0 |

Figure 6:
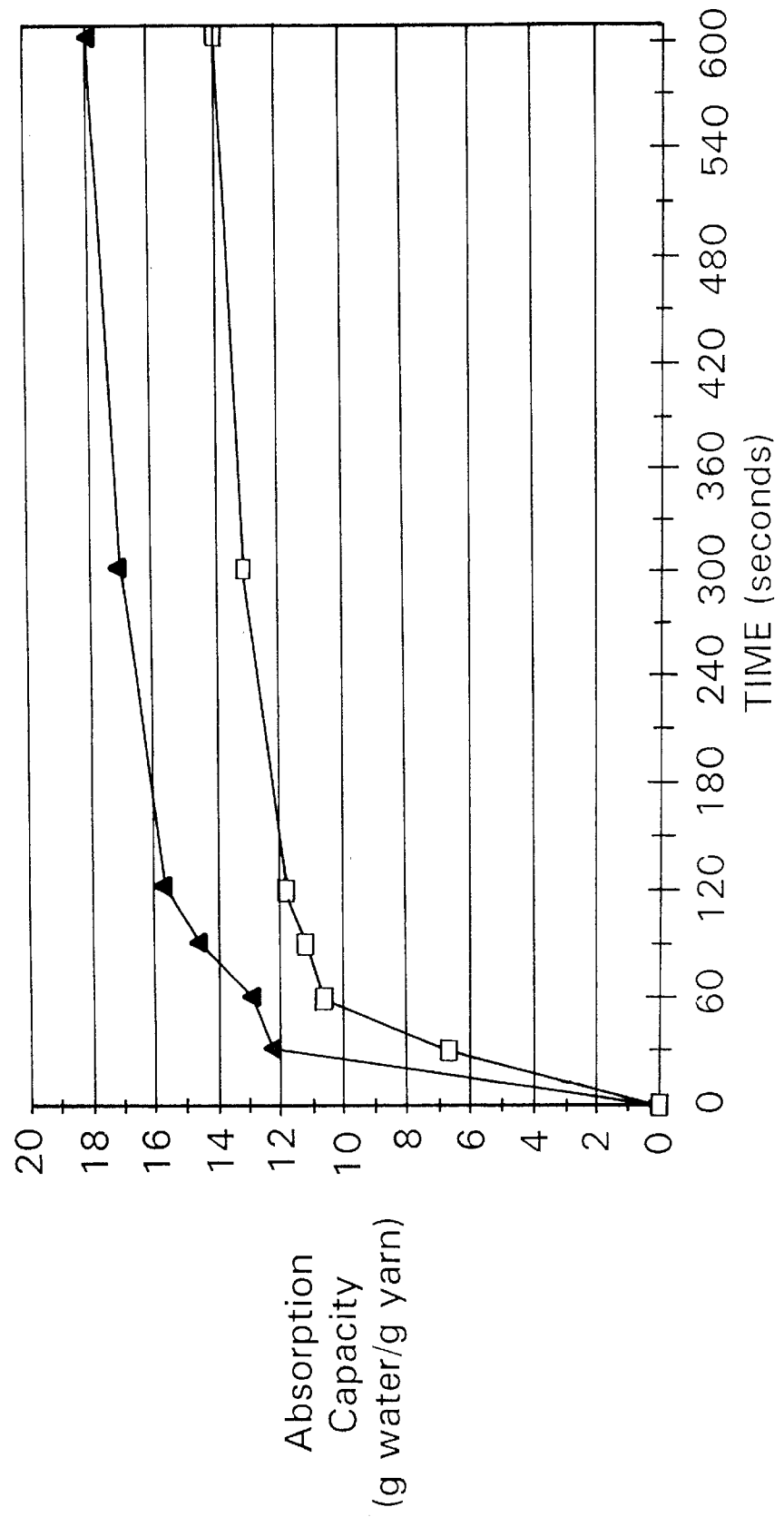
FIG. 6 is a plot of absorption capacity of water swellable coated polyester yarn in tap water against time for both a prior art fully fused coating —■— and a semi-gel coating —▲— according to the invention.

While the effect of the tap water electrolytes can be seen by comparing the data of Table I and Table III, it is clear from the data in Table III and FIG. 6, that the Experimental Samples 12–17 still show a significant increase in absorption rate and capacity in comparison with prior art coatings of Comparative Samples 12–17. It took over 600 s for the Comparative Samples to reach their maximum absorption capacity of 14.0, whereas the Experimental Samples reached a 14.0 absorption capacity in only 80 s and continued on to a maximum of 18.0, i.e., 28.5% greater. In applications where the speed of absorption is critical, such as for water-blocking of coaxial or fiber optic cable, this increase in absorption rate is highly significant. Based on Table III, it can be seen that even in brackash waters where electrolytes play a role, a significant increase in absorption capacity is achieved.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A water swellable coating, comprising a semi-gel dispersion of a particulate superabsorbent polymer which is hydrophilic and capable of absorbing and retaining a large quantity of water in a polyvinyl chloride plastisol.

2. The water swellable coating according to claim 1, wherein the particulate superabsorbent polymer is selected from the group consisting of at least partially cross-linked homopolymers and copolymers of sodium polyacrylate, and potassium polyacrylate.

3. The water swellable coating according to claim 2, wherein the particulate superabsorbent polymer is sodium polyacrylate homopolymer having an average particle size of from about 1 to about 500 microns.

4. The water swellable coating according to claim 3, wherein the particulate superabsorbent polymer is sodium polyacrylate homopolymer having an average particle size of from about 1 to about 100 microns.

5. The water swellable coating according to claim 2, wherein the particulate superabsorbent polymer is a potassium copolymer of polyacrylate and polyacrylamide having an average particle size of from about 1 to about 500 microns.

6. The water swellable coating according to claim 1, wherein the polyvinyl chloride plastisol comprises a polyvinyl chloride resin and a plasticizer, the weight percentage ratio of the resin to the plasticizer being from about 0.25:1 to about 3:1.

7. The water swellable coating according to claim 6, wherein the weight percentage ratio of the resin to the plasticizer is about 1:1.

8. The water swellable coating according to claim 5, wherein the plastisol further comprises an additive selected from the group consisting of secondary plasticizers, flame retardants, stabilizers, fillers, colorants, viscosity modifiers, foaming agents and combinations thereof.

9. The water swellable coating according to claim 1, wherein the coating comprises from about 10 weight percent to about 50 weight percent superabsorbent polymer.

10. The water swellable coating according to claim 1, wherein the absorption capacity of the coating is at least about 34 g water/g coating after a 5 minute exposure of a 0.011 inch thick layer of the coating to distilled water.

11. The water swellable coating according to claim 10, wherein the absorption capacity of the coating is at least about 40 g water/g coating after a 5 minute exposure of a 0.011 inch thick layer of the coating to distilled water.

* * * * *